United States Patent [19]

Nakao et al.

[11] Patent Number: 5,336,227

[45] Date of Patent: Aug. 9, 1994

[54] SURGICAL CAUTERIZATION SNARE WITH POLYP CAPTURING WEB NET

[75] Inventors: Naomi L. Nakao; Peter J. Wilk, both of New York, N.Y.

[73] Assignee: Wilk & Nakao Medical Technology Incorporated, New York, N.Y.

[21] Appl. No.: 12,657

[22] Filed: Feb. 1, 1993

Related U.S. Application Data

[63] Continuation-in-part of Ser. No. 788,035, Nov. 5, 1991, Pat. No. 5,201,740, and a continuation-in-part of Ser. No. 892,214, Jun. 2, 1992, Pat. No. 5,190,542.

[51] Int. Cl.$^5$ ............................................... A61B 17/00
[52] U.S. Cl. .................................... 606/114; 606/110; 606/113; 128/4
[58] Field of Search ................. 128/4, 6; 604/93, 171, 604/264; 606/37, 39, 40, 41–52, 106, 110, 113, 114, 127, 128, 170, 167

[56] References Cited

U.S. PATENT DOCUMENTS

| | | | |
|---|---|---|---|
| 460,940 | 10/1891 | Baugh | 606/106 |
| 1,609,014 | 11/1926 | Dowd | 606/114 |
| 3,472,230 | 10/1969 | Fogarty | 606/127 |
| 3,715,829 | 2/1973 | Hamilton . | |
| 4,202,338 | 5/1980 | Bitrolf | 606/47 |
| 4,326,530 | 4/1982 | Fleury, Jr. | 606/47 |
| 4,345,599 | 8/1982 | McCarrell | 606/113 |
| 4,493,320 | 1/1985 | Treat | 606/47 |
| 4,503,855 | 3/1985 | Maslanka | 606/47 |
| 4,516,347 | 5/1985 | Dickie . | |
| 4,557,255 | 12/1985 | Goodman | 606/127 |
| 4,638,802 | 1/1987 | Okada | 606/47 |
| 4,643,187 | 2/1987 | Okada | 606/47 |
| 4,718,419 | 1/1988 | Okada | 128/4 |
| 4,997,435 | 3/1991 | Demeter | 606/127 |
| 5,037,379 | 8/1991 | Clayman et al. . | |
| 5,084,054 | 1/1992 | Bencini et al. | 606/127 |
| 5,122,147 | 6/1992 | Sewell | 606/113 |
| 5,143,082 | 9/1992 | Kindberg et al. . | |
| 5,147,371 | 9/1992 | Washington et al. . | |
| 5,158,561 | 10/1992 | Rydell et al. . | |
| 5,190,542 | 3/1993 | Nakao et al. | 606/113 |
| 5,201,740 | 4/1993 | Nakao et al. | 606/113 |

FOREIGN PATENT DOCUMENTS

| | | | |
|---|---|---|---|
| 0025796 | 1/1884 | Brazil | 606/127 |
| 0046856 | 5/1889 | Fed. Rep. of Germany | 606/45 |

OTHER PUBLICATIONS

Waye, J. D. et al., "The Lost Polyp: a Guide to Retrieval during Colonoscopy" *Int. J. Colorect Disc* (1988) 3:229–231.

Ricca, J. J. "Retrieval of Polyps Severed at Colonoscopy" *Gastrointestinal Endoscopy* (1977) 24, 1:44.

Maas, L. C. et al. "Polyp Retrieval Impossible Without Colonoscope Tip" and Ward, W. J. Reply *Gastrointestinal Endoscopy* (1984) 30, 6:378.

(List continued on next page.)

*Primary Examiner*—Stephen C. Pellegrino
*Assistant Examiner*—Glenn K. Dawson
*Attorney, Agent, or Firm*—R. Neil Sudol; Henry D. Coleman

[57] ABSTRACT

A surgical instrument assembly for use in snare cauterization operations includes a tubular sheath member, a metallic cauterization loop, and a metal wire operatively connected to the loop, the wire passing longitudinally through the sheath. An electrical supply is operatively connectable to the wire for feeding an electrical current to the loop via the wire, while a manually actuatable shifter is operatively connected to the wire for longitudinally sliding the wire along the sheath in alternately opposite directions. A flexible web member is connected to the loop to form a capture pocket, the loop defining a mouth opening of the pocket. During use of the snare cauterization instrument, the loop is at least partially expanded from a collapsed configuration and passed over a polyp to be removed, so that the web member substantially surrounds the selected polyp. The loop is then closed to engage the polyp around a base region thereof and an electrical current is subsequently conducted through the loop to burn through the polyp at the base region thereof. Severance of the polyp occurs upon a closure of the cauterization loop by its being withdrawn or retracted into the tubular sheath member. The severed polyp is automatically captured by the web member.

20 Claims, 8 Drawing Sheets

OTHER PUBLICATIONS

Abrams, J. S. "A Hard Look at Colonoscopy" *The American Journal of Surgery* (Jan. 1977) 133:111–115.

Schwesinger, W. H. "Complications in Colonoscopy" *Surgery, Gynecology & Obstetrics* (Feb. 1979) 148:270–281.

Sugarbaker, P. H. "Colonoscopy in the Management of Diseases of the Colon and Rectum" *Surgery, Gynecology & Obstetrics* (Sep. 1974) 139:341–349.

Kobayashi, S. "Colonoscopic Polypectomy With Special Reference To Management of Multiple Polyps" (Kitano H. et al.) *Gastro Endosc* (1983) 29, 4:335–6.

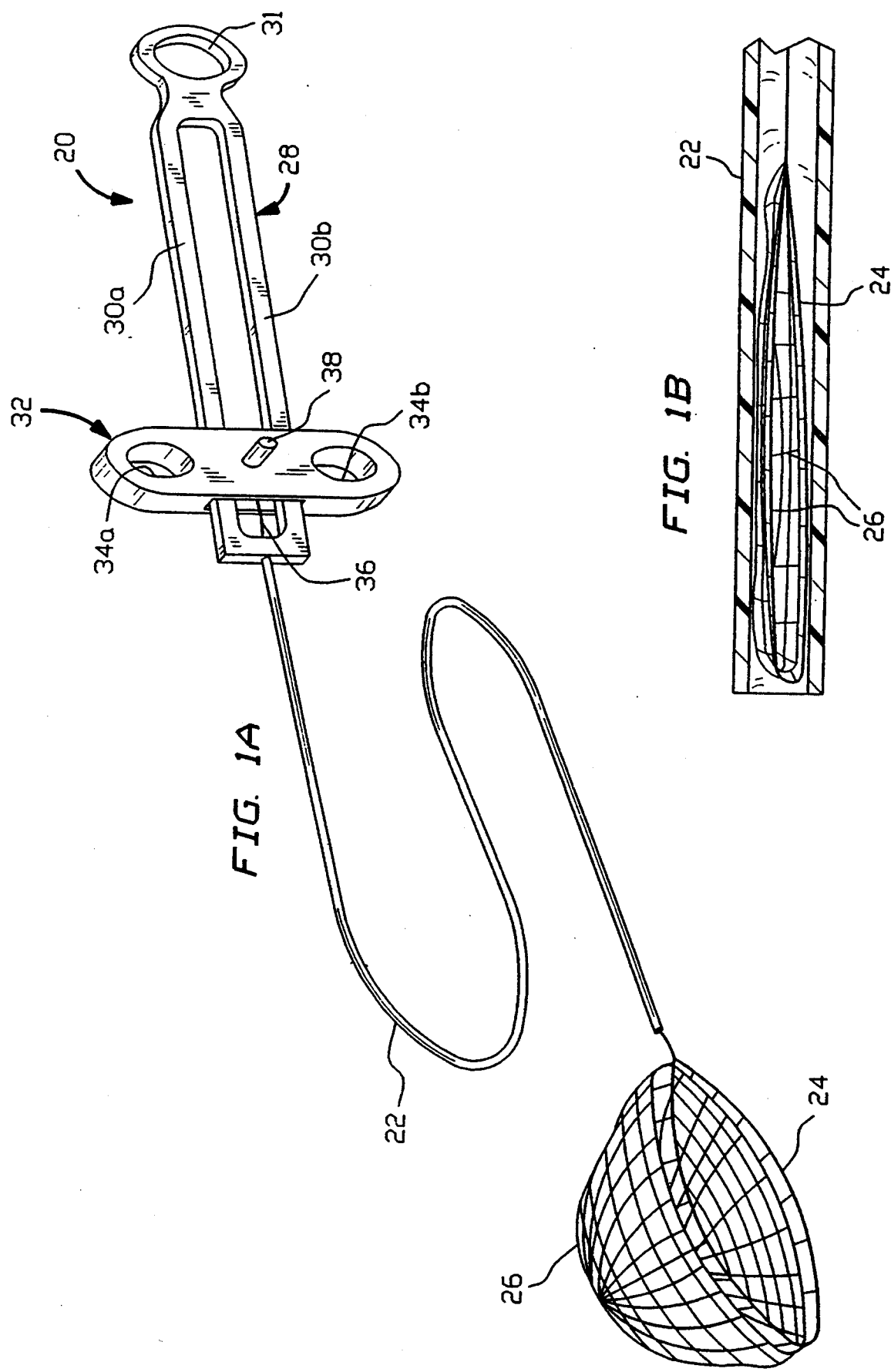

SURGICAL CAUTERIZATION SNARE WITH POLYP CAPTURING WEB NET

CROSS-REFERENCE TO RELATED APPLICATION

This application is a continuation-in-part of commonly owned application Ser. No. 788,035 filed Nov. 5, 1991, now U.S. Pat. No. 5,201,740, and a continuation-in-part of commonly owned application Ser. No. 892,214 filed Jun. 2, 1992, now U.S. Pat. 5,180,542.

FIELD OF THE INVENTION

This invention relates to a surgical instrument assembly for use in retrieving objects from internal body cavities. This invention also relates, more specifically, to a surgical instrument assembly for use in snare cauterization operations. This invention also relates to a related method for retrieving objects from internal body cavities and more particularly to a method for capturing and/or retrieving polyps and other clumps of organic tissue which have been severed from a patient's internal organs via a snare cauterization technique.

BACKGROUND OF THE INVENTION

In a conventional snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmittted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In extreme cases, the endoscope must be removed without the polyp and the patient given an enema in an attempt to flush out the polyp from the colon.

Furthermore, there are numerous cases where a severed polyp is never recovered. Sometimes, the polyp is masserated during the retrieval attempt. In all such cases, the pathologist is unable to determine whether the polyp contains carcinoma in situ (localized) or infiltrative carcinoma (spread). The patient must then undergo a colon ressection, sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

OBJECTS OF THE INVENTION

An object of the present invention is to provide an improved method for the removal of portions of internal body organs or other objects from patients.

A more specific object of the present invention is to provide an improved method for the performance of snare cauterization.

Another object of the present invention is to provide a snare cauterization technique wherein the capture and retrieval of severed polyps is facilitated.

Another, more particular, object of the present invention is to provide a snare cauterization technique wherein trauma to the patient and time in surgery are reduced.

A further object of the present invention is to provide an instrument assembly for use in removing portions of body organs or other objects from patients.

Yet another, more particular, object of the present invention is to provide such an instrument assembly which facilitates the capture and retrieval of severed polyps and other clumps of severed body tissues from the internal cavities of patients.

Another particular object of the present invention is to provide such an instrument assembly which is simple to manufacture and therefore inexpensive.

A further particular object of the present invention is to provide such an instrument assembly which is easy to use.

An additional particular object of the present invention is to provide such an instrument assembly which is disposable. Such an instrument assembly requires no lengthy sterilization procedure and reduces the spread of infectitous diseases such as AIDS.

These and other objects will be apparent from the following descriptions.

SUMMARY OF THE INVENTION

In a method for removing a selected portion of internal body tissues of a patient in accordance with the present invention, a conductive cauterization loop is provided to which a flexible web member is connected to define an expandable pocket, the web member being attached to the loop in a manner so as to expose the loop to enable effective cauterization of organic tissues by the loop. Other steps of the method include (a) inserting an endoscope assembly into a patient, (b) using the endoscope assembly to visually monitor internal body tissues of the patient upon insertion of the endoscope assembly into the patient, (c) ejecting the loop with the web member from a distal end of a biopsy channel of the endoscope assembly upon detecting selected internal body tissues to be removed from the patient, (d) at least partially expanding the loop and the web member from a collapsed configuration upon ejection of the loop and the web member from the biopsy channel, and (e) manipulating the loop from outside of the patient, e.g., via the endoscope assembly and more particularly via an elongate wire or tubular sheath member extending through the biopsy channel of the endoscope assembly. The loop is manipulated to pass the expanded loop over the selected internal body tissues to be removed, so that the web member substantially surrounds the selected internal body tissues. Subsequent steps of the method include (f) closing the loop to engage the selected internal body tissues around a base region thereof, (g) conducting an electrical current through the loop to burn through the selected internal body tissues at the base region, thereby severing the selected internal body tissues at the base region, and (h) at least partially closing the loop upon a completed burning of the loop through the base region, thereby capturing the severed internal body tissues.

According to another feature of the present invention, the method further comprises the steps of (i) ejecting an auxiliary-instrument from a distal end of the endoscope assembly and (j) operating the auxiliary instrument to apply a pair of markers to tissues on opposite sides of the base region, thereby enabling subsequent identification of the severed internal body tissues with a respective site within the patient. The markers may be a biocompatible dye or ink. In that event, the dye or ink may be injected into the tissues or may be painted (sprayed, brushed) onto the tissue surfaces.

Alternatively, color markers may be applied by transferring a color patch from the loop during the conduction of current therethrough. The markers may be made of a hued material which liquifies at a predetermined temperature and is absorbable by organic tissues.

The use of markers in accordance with the present invention enables the removal of multiple polyps or other tissue growths during a single endoscopic insertion procedure. Several severed polyps may be removed and captured in the same retrieval net, without necessitating a removal of the entire endoscope assembly between successive polyp cuts. Subsequently, if one polyp is identified as being malignant or a potential carcinoma, another endoscopic examination may be undertaken with a quick and easy identification of the site of interest in the colon or other cavity.

An associated surgical instrument assembly for use in snare cauterization operations comprises, in accordance with the present invention, an endoscope assembly including a biopsy channel and means at a distal end of an endoscope insertion member for delivering light to and receiving light from a surgical site. A tubular sheath member is inserted through the biopsy channel, while a metal wire operatively connected to a metallic cauterization loop passes longitudinally through the sheath. An electrical supply is operatively connected to the wire for feeding an electrical current to the loop via the wire, and a manually actuatable shifter is operatively connected to the wire for longitudinally sliding the wire along the sheath in alternately opposite directions. A flexible web member is connected to the loop to form a capture pocket, the loop defining a mouth opening of the pocket. The web member is attached to the loop in a manner so as to expose the loop to enable effective cauterization of organic tissues by the loop.

According to an additional feature of the present invention, the loop opens and closes in essentially a single plane and has a bend in an expanded configuration of the loop, the bend arcing out of the plane of expansion and contraction. The bend enhances manueverability of the loop, thereby facilitating isolation and capture of polyps of a wide range of sizes and shapes.

An identification device may be ejectable in part from a distal end of the endoscope assembly for applying a pair of markers to tissues on opposite sides of the base region, thereby enabling subsequent identification of the severed internal body tissues with a respective site within the patient. The identification device may operate to apply a biocompatible dye or ink to tissues on opposite sides of the base region of the polyp or tissue growth.

Alternatively, a patch of liquifiable material (e.g., in the form of a ring) may be attached to the loop for transferring color from the loop to tissues on opposite sides of the base region of the polyp or tissue growth during the conduction of electrical current through the cauterization loop.

A method for removing a selected portion of internal body tissues of a patient comprises, in accordance with another conceptualization of the present invention, the steps of (i) providing a conductive cauterization loop to which a flexible web member is connected to define an expandable pocket, the web member being attached to the loop in a manner so as to expose the loop to enable effective cauterization of organic tissues by the loop, (ii) at least partially expanding the loop and the web member from a collapsed configuration, passing the expanded loop over the selected internal body tissues to be removed, so that the web member substantially surrounds the selected internal body tissues, (iii) closing the loop to engage the selected internal body tissues around a base region thereof, (iv) conducting an electrical current through the loop to burn through the selected internal body tissues at the base region, thereby severing the selected internal body tissues at the base region, and (v) operating an instrument to apply a pair of markers to tissues on opposite sides of the base region, thereby enabling subsequent identification of the severed internal body tissues with a respective site within the patient.

The markers may be colored staples, the step of operating the instrument including the step of applying the staples to the tissues on opposite sides of the base region of the polyp of tissue growth. The staples may be applied before or after the placement of the capture net about the polyp.

Color markers may be applied to organic tissues in the patient by injecting the biocompatible dye or ink into the tissues or by painting a colored substance onto the tissues.

A surgical assembly comprises, in accordance with a particular embodiment of the present invention, a tubular sheath member and a metallic cauterization loop. The loop is alternately contractible and expandable in essentially a single plane and has a bend in an expanded configuration of the loop. The bend arcs out of the expansion and contraction plane in the expanded configuration of the loop. A metal wire is operatively connected to the loop and passes longitudinally through the sheath, while an electrical supply is operatively connected to the wire for feeding an electrical current to the loop via the wire. A manually actuatable shifter is operatively connected to the wire for longitudinally sliding the wire along the sheath in alternately opposite directions, and a flexible web member is connected to the loop to form a capture pocket, the loop defining a mouth opening of the pocket. The web member is attached to the loop in a manner so as to expose the loop to enable effective cauterization of organic tissues by the loop.

The present invention provides an improved method for the removal of portions of internal body organs from patients via snare cauterization.

In a method in accordance with the present invention, the capture and retrieval of severed polyps is facilitated. An instrument assembly in accordance with the present invention is simple to use. Accordingly, trauma to the patient and time in surgery are reduced. More specifically, time under anaesthesia with the accompanying side effects is reduced. Concomitantly, the expense of hospitalization is decreased.

BRIEF DESCRIPTION OF THE DRAWING

FIG. 1A is a schematic perspective view of a snare cauterization instrument assembly in accordance with the present invention, showing a cauterization loop in an ejected, use configuration.

FIG. 1B is a schematic longitudinal cross-sectional view of a distal end of the cauterization instrument assembly of FIG. 1A, showing the cauterization loop in a withdrawn or retracted storage configuration inside the distal end of a tubular member of the instrument assembly.

DETAILED DESCRIPTION

Figure 2A:
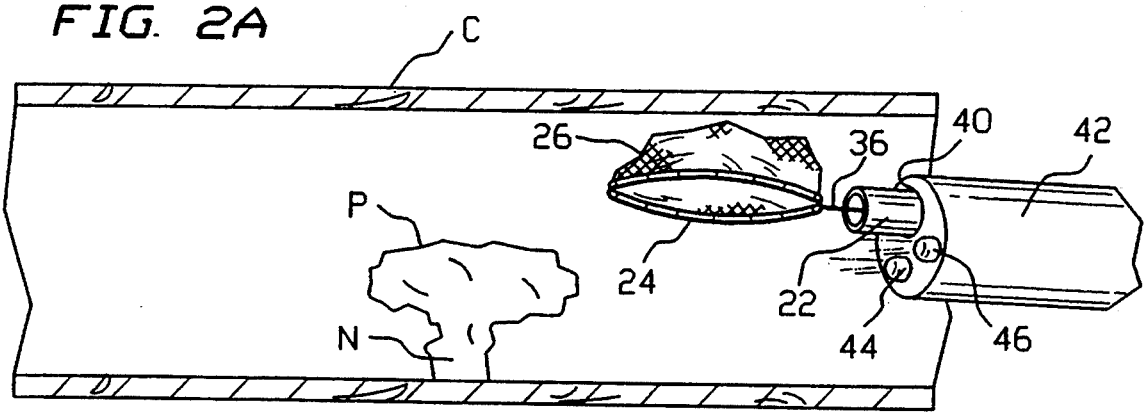
FIG. 2A is a schematic partial cross sectional view of a patient's colon with a polyp, showing the snare cauterization instrument assembly of FIG. 1A inserted in the biopsy channel of an endoscope which is itself inserted into the patient's colon, and further showing the instrument assembly in an initial stage of a snare cauterization procedure.

As illustrated in FIG. 1A, a snare cauterization instrument assembly comprises a hand held control module 20, a flexible tubular member 22 connected to a distal end of the control module, and an alternately expandable and closable cauterization loop 24 at the distal tip of the flexible tubular member 22. A flexible sheet or web 26 specifically in the form of a net is attached to cauterization loop 24 for defining a capture pocket. Loop 24 defines the mouth of the capture pocket.

Control module 20 comprises a body member or frame 28 which includes a pair of parallel rails 30a and 30b to which a slider member 32 is reciprocatably secured. Frame 28 has a thumb hole 31 at a proximal end, whereas slider member 32 has a pair of finger holes 34a and 34b and is fastened to the proximal end of a wire 36 which passes through tubular member 22 and is in turn connected to cauterization loop 24 at the distal end of tubular member 22. Wire 36 is sufficiently flexible to bend with tubular member 22 during the negotiation thereby of curves or bends in a colon during surgery.

Slider member 32 is also provided with an electrical connector 38 which is couplable to a source of electrical energy. During a severing step of a cauterization operation, described in detail hereinafter with reference to FIG. 2E, electrical energy is fed to loop 24 via connector 38 and wire 36.

Capture web 26 is thin and flexible and preferably made of biologically inert flexible transparent synthetic resin or polymeric material such as polyethylene or nylon. Prior to the beginning of a snare cauterization operation, web 26 is disposed in a closed, folded or contracted state, together with loop 24, in the distal end of tubular member 22, as illustrated in FIG. 1B. Concomitantly, slider member 32 is retracted to the proximal end of rails 30a and 30b (towards the right side of frame 28 in FIG. 1A). Tubular member 22 is inserted in a biopsy channel 40 of an endoscope 42, as shown in FIG. 2A, and the endoscope is inserted into a body cavity of a patient, such as a colon C.

As illustrated further in FIG. 2A, endoscope 42 is conventionally provided at its distal end with a pair of apertures 44 and 46 for respectively delivering light to and receiving light from a surgical site.

Upon the discovery of a polyp P within colon C via the use of endoscope 42, the snare cauterization instrument assembly is shifted in a distal direction so that tubular member 22 protrudes from the distal end of biopsy channel 40. Then, slider member 32 is shifted in a distal direction to eject loop 24 and capture web 26 from tubular member 22. Upon ejection, loop 24 and capture web 26 expand from a contracted or closed configuration into an at least partially opened configuration, as shown in FIG. 2A.

Figure 2B:
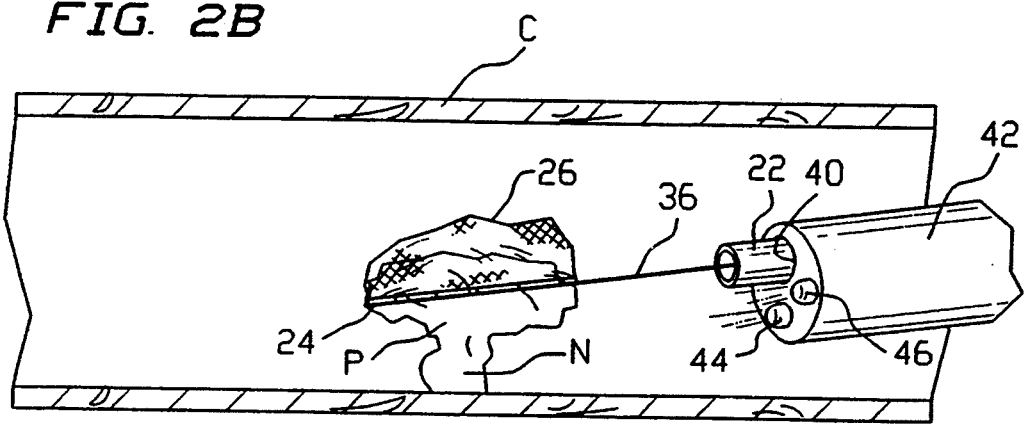
FIG. 2B is a schematic partial cross sectional view similar to FIG. 2A, showing a loop of the snare cauterization instrument assembly of FIG. 1A being passed around the polyp of FIG. 2A.
Figure 2C:
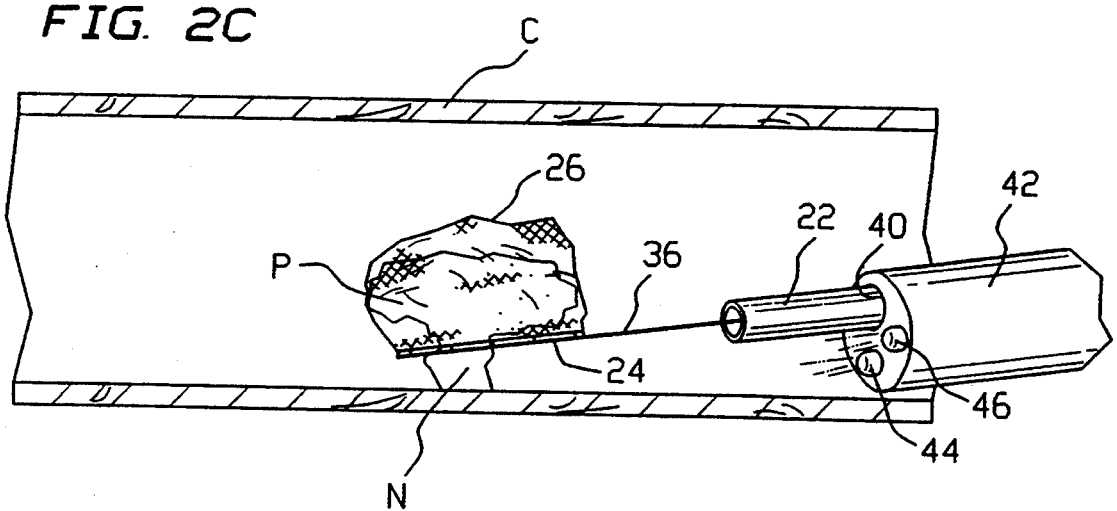
FIG. 2C is a schematic partial cross sectional view similar to FIGS. 2A–2B, showing the loop of the snare cauterization instrument assembly of FIG. 1A completely passed around the polyp of FIG. 2A.

FIG. 2B depicts a later stage in the cauterization procedure. The snare cauterization instrument assembly of FIG. 1A is manipulated to pass loop 24 around polyp P, with capture web 26 following. Eventually, loop 24 encircles a base region or neck N of polyp P and the polyp is surrounded by capture web 26, as shown in FIG. 2C.

Figure 2D:
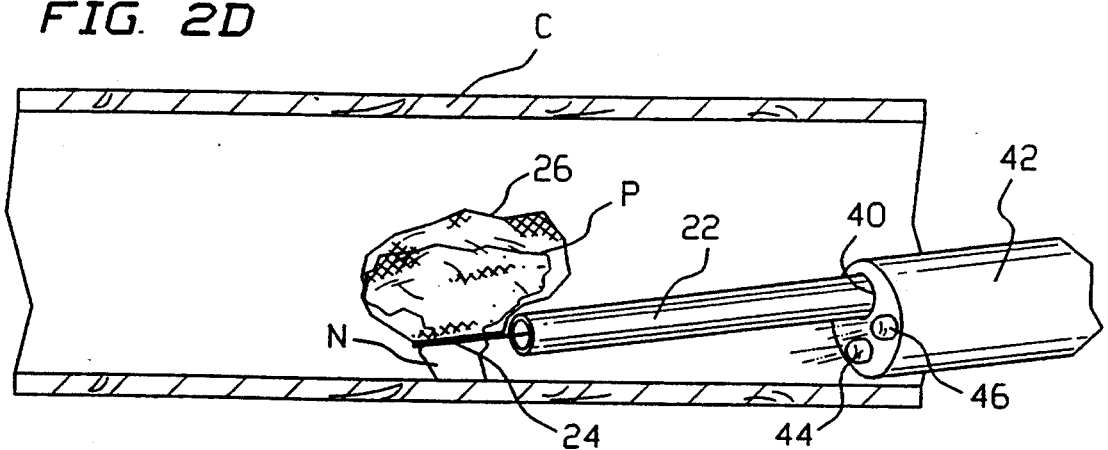
FIG. 2D is a schematic partial cross sectional view similar to FIGS. 2A–2C, showing the loop of the snare cauterization instrument assembly of FIG. 1A being tightened around a base or neck of the polyp.

At that juncture, slider member 32 is pulled back in the proximal direction, whereby wire 36 pulls loop 24 partially back into the distal end of tubular member 22, thereby causing loop 24 to tighten about neck N of polyp P, as illustrated in FIG. 2D.

Figure 2E:
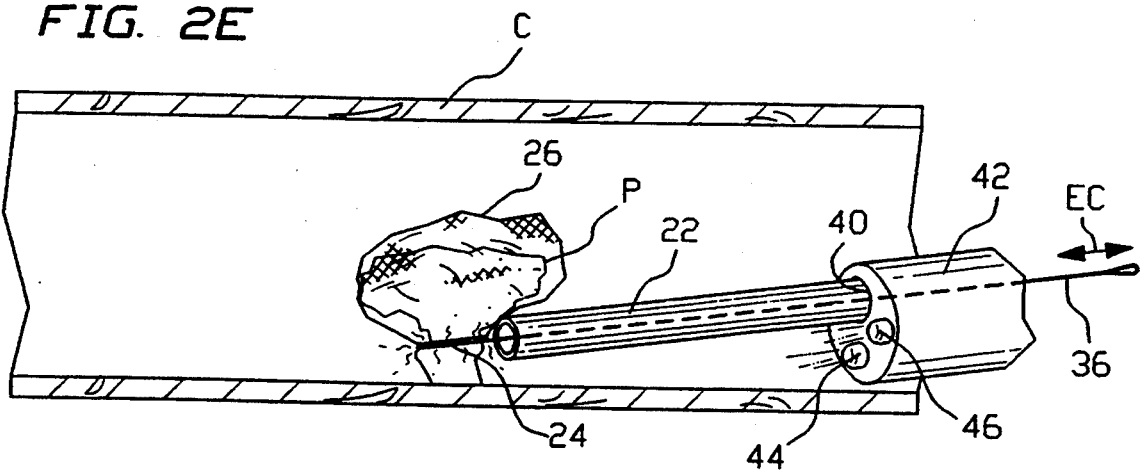
FIG. 2E is a schematic partial cross sectional view similar to FIGS. 2A–2D, showing the loop of the snare cauterization instrument assembly of FIG. 1A in an electrically energized state for burning through the base or neck of the polyp.
Figure 2F:
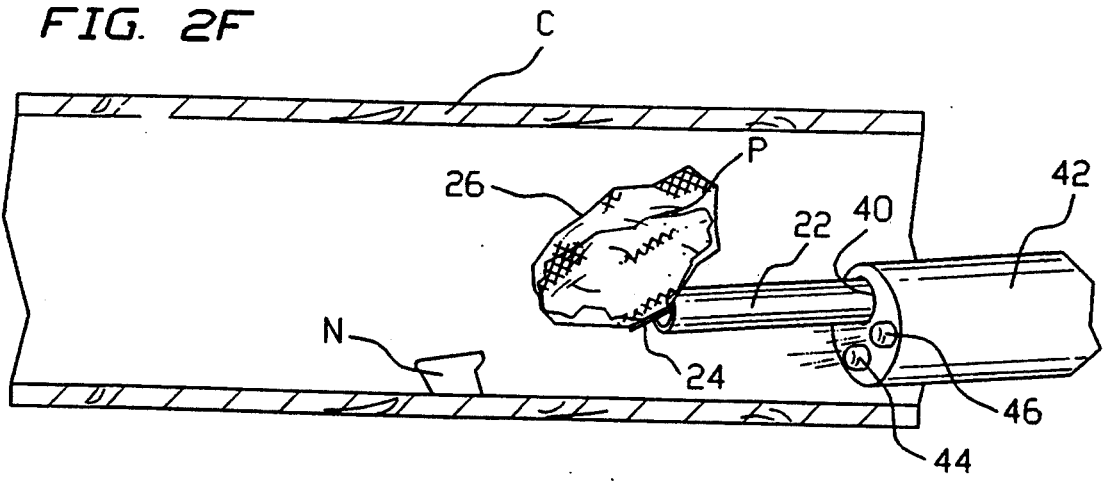
FIG. 2F is a schematic partial cross sectional view similar to FIGS. 2A–2E, showing the polyp severed from the colon wall and captured with the snare cauterization instrument assembly of FIG. 1A.
Figure 2G:
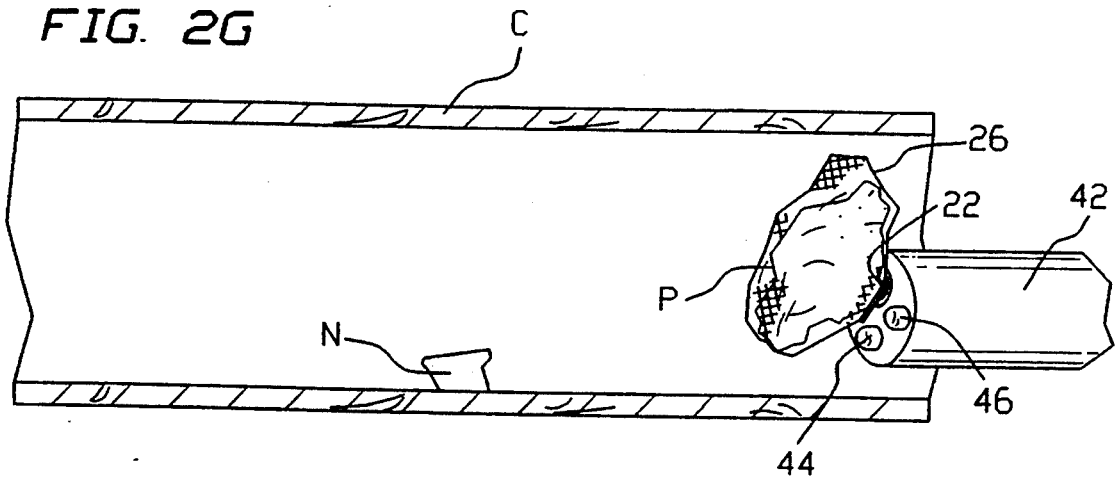
FIG. 2G is a schematic partial cross sectional view similar to FIGS. 2A–2G, showing the snare cauterization instrument assembly of FIG. 1A together with the captured polyp drawn towards the distal end of the endoscope.

As indicated in FIG. 2E, electrical current EC is then caused to pass through wire 36 and loop 24. Generally, electric correct from loop 24 is conducted through neck N of polyp P, thereby generating in the polyp tissues heat sufficiently great to sever and cauterize neck N. Upon the severing of polyp P at neck N, slider member 32 is pulled farther in the proximal direction, thereby pulling loop 24 further into the distal end of tubular member 22, as shown in FIG. 2F, to essentially close the loop. Polyp P is now securely trapped in capture web 26. In a further step, depicted in FIG. 2G, the entire snare cauterization instrument assembly including, in particular, tubular member 22, is shifted in the proximal direction relative to endoscope 42. However, care is taken not to draw the distal end of tubular member 22 and particularly capture web 26 with polyp P back into biopsy channel 40 of the endoscope. Polyp P remains in web or capture pocket 26 outside of tubular member 22 and endoscope 42 during the withdrawal of endoscope 42 from the patient.

Every polyp severed by a snare cauterization instrument as described and illustrated herein is captured immediately. Thus, the time for the capture and retrieval of severed polyps is reduced to a minimum. Trauma to patient is likewise reduced, as are hospitalization expenses.

Figure 3:
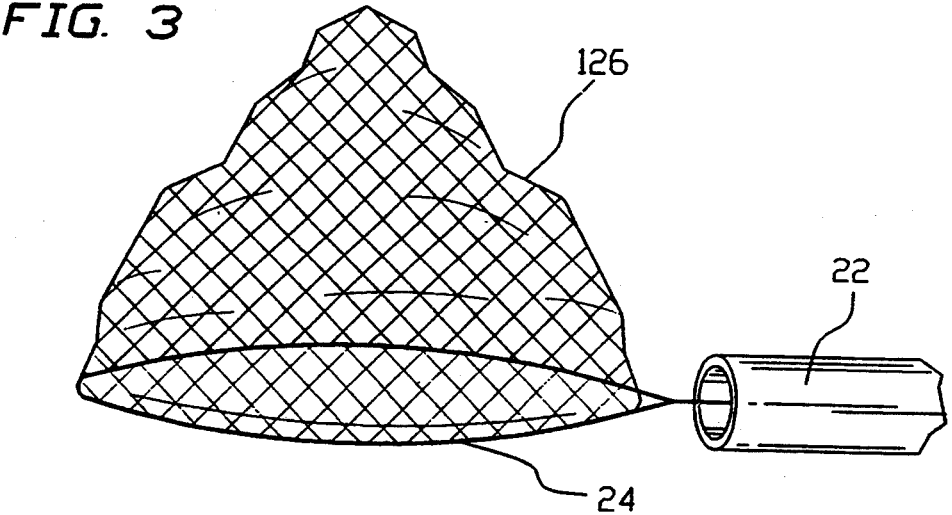
FIGS. 3–6 are schematic partial side perspective views, showing different specific embodiments of a snare cauterization instrument assembly in accordance with the present invention.
Figure 4:
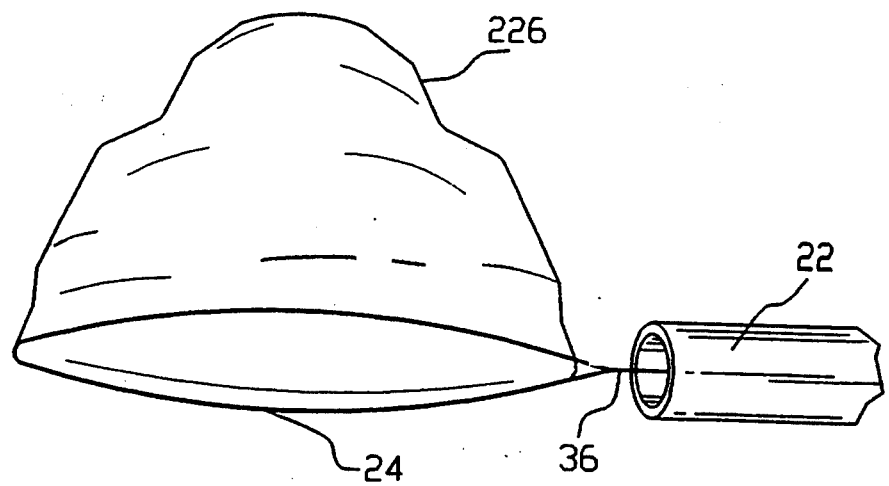
Figure 5:
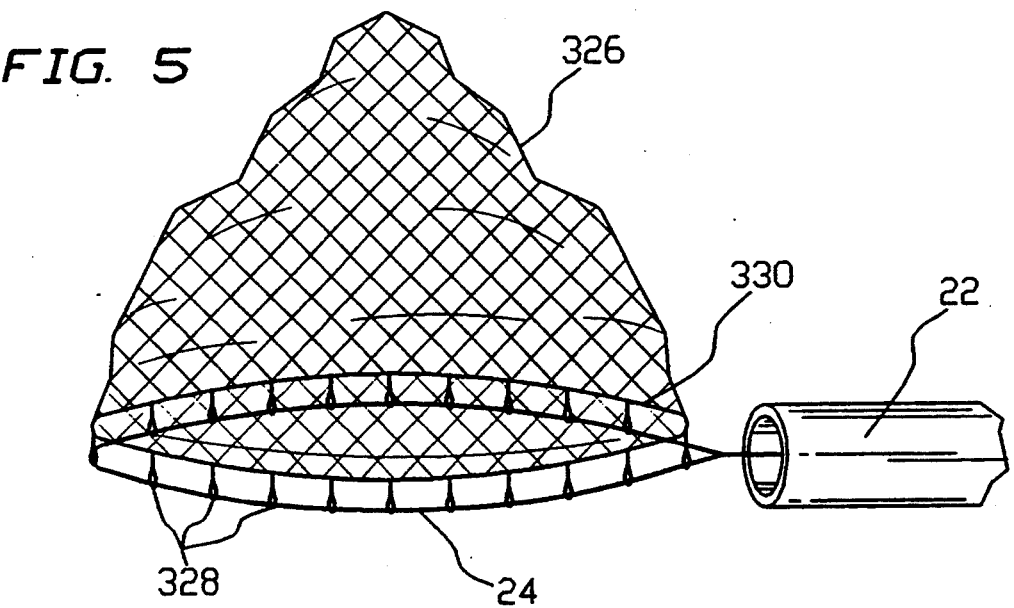
Figure 6:
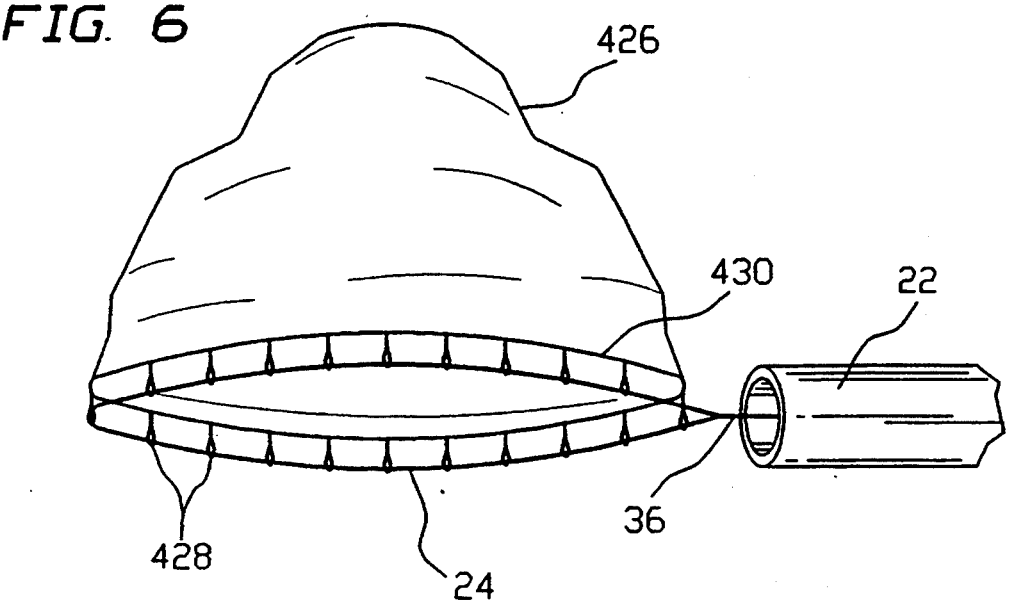

In FIGS. 3-6, like structural components bear the same reference designations. FIG. 3 shows a capture web 126 in the form of a net fastened directly to loop 24, while FIG. 4 shows a capture web 226 in the form of a continuous or solid transparent film fastened directly to loop 24. FIG. 5 illustrates a capture web 326 in the form of a net attached to loop 24 via a multiplicity of spaced ringlets 328. Loop 24 passes through ringlets 328, which are connected to a ring-shaped rim element 330 of web 326. Ringlets 328 are preferably made of a metallic material to facilitate the transmission of electrical current from cauterization loop 24 to the tissues of a polyp. FIG. 6 shows a capture web 426 in the form of a continuous or solid film of transparent polymeric material attached to loop 24 via a multiplicity of spaced ringlets 428. Loop 24 passes through ringlets 428, which are connected to a ring-shaped rim element 430 of web 326.

Figure 7:
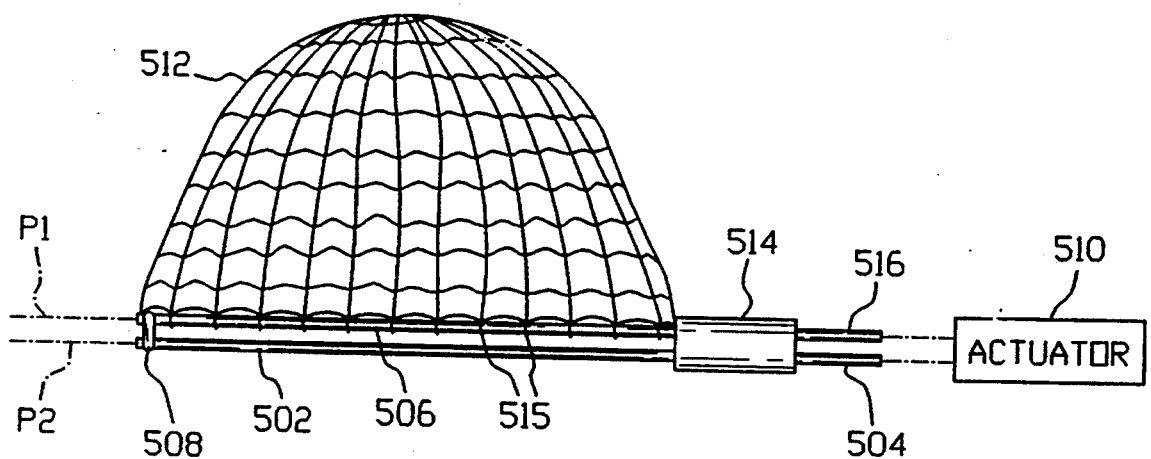
FIG. 7 is a schematic side elevational view, on an enlarged scale, of another embodiment of a snare cauterization instrument assembly, showing a pocket-defining web member on an auxiliary loop.

As illustrated in FIG. 7, a snare cauterization instrument assembly comprises a flexible cauterization loop 502, an electrical conductor 504 operatively connected to the cauterization loop for feeding an electrical current thereto, and a flexible auxiliary loop 506 connected via a fastening element 508 to the cauterization loop only at a distal end thereof. An actuator 510 is operatively connected to cauterization loop 502 and auxiliary loop 506 for alternately expanding and contracting the two loops in tandem with one another. A flexible web member 512 in the form of a net (or a continuous transparent membrane) is connected to auxiliary loop 506 essentially around the circumference thereof to form a capture pocket, auxiliary loop 506 defining a mouth opening of the pocket. Preferably, net 512 is fixed to auxiliary loop 506 only at a distal end and a proximal end (inside a tubular sheath member 514) thereof, the remaining connections 515 being slidable.

Actuator 510 is connected to cauterization loop 502 via conductor 504, which functions in response to manipulations of actuator 510 to eject cauterization loop 502 from a collapsed storage position inside the distal end of tubular sheath member 514 and subsequently to pull cauterization loop back into the sheath member. Actuator 510 is coupled to auxiliary loop 506 via a flexible wire or rod member 516 which like conductor 504 extends longitudinally through sheath member 514.

Figure 8:
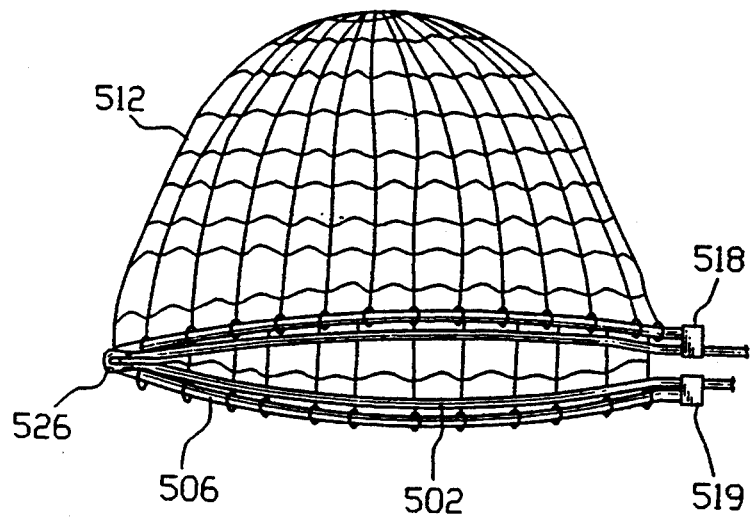
FIG. 8 is a schematic perspective view, also on an enlarged scale, of a modified snare cauterization instrument assembly, showing an auxiliary loop attached at three points to a cauterization loop.

Cauterization loop 502 and auxiliary loop 506 are disposed in parallel planes P1 and P2, respectively. As depicted in FIG. 8, auxiliary loop 506 may be connected at a proximal end to cauterization loop 502 at two points 518 and 519, as well as to the distal end of the cauterization loop. In that event, wire or rod member 516 may be omitted. As further shown in FIG. 8, auxiliary loop 506 is slightly larger than cauterization loop 502. The loops 502 and 506 are close, almost touching one another. As described above with reference to FIG. 7, web member 512 is fixedly connected to auxiliary loop 506 at a distal end and a proximal end thereof and slidably connected to the auxiliary loop between those ends.

Figure 9:
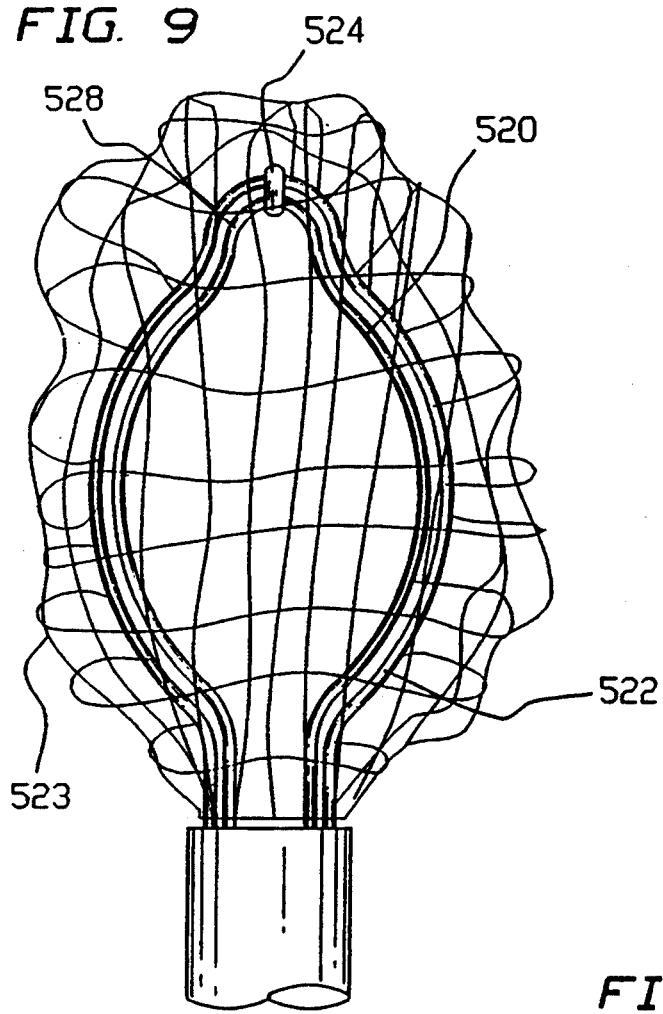
FIG. 9 is a schematic top view of another modified snare cauterization instrument assembly, showing an auxiliary loop attached at one point to a cauterization loop.

FIG. 9 shows a cauterization loop 520 and an auxiliary loop 522 connected to one another at a distal end via a fastener 524. Cauterization loop 520 and auxiliary loop 522 are essentially coplanar in the expanded configuration illustrated in FIG. 9. During an ejection stroke and a subsequent retraction stroke of cauterization loop 520 and auxiliary loop 522 in response to the manipulations of an actuator (not shown) at a proximal end (not shown) of the instrument assembly, cauterization loop 520 and auxiliary loop 522 expand and contract in unison in essentially a common plane.

The embodiments of a cauterization snare instrument assembly illustrated in FIGS. 7–9 are less expensive to manufacture than the ringlet embodiments of FIG. 5 and 6 and enable use of a wider range of materials for the pocket or web member (512 in FIG. 7) than the embodiments of FIGS. 3 and 4. In addition, a primary advantage of the particular dual loop embodiments of FIGS. 7–9 is that auxiliary loops 506 and 522 are not connected to the cauterization loops 502 and 520 along operative portions thererof, thereby eliminating any possible interference that the auxiliary loops or capture nets 512 and 523 (FIG. 9) might otherwise exhibit with respect to the cutting and cauterization operations.

As illustrated in FIGS. 8 and 9, this elimination of possible interference in the cutting and cauterization operations is furthered by forming cauterization loops 502 and 520 at their distal ends with respective tongue-like extensions 526 and 528 to which auxiliary loops 506 and 522 are connected. Extensions 526 and 528 may be coated with an insulating material (not illustrated) and serve to separate fasteners 508 and 524 from the site of the cauterization procedure.

Auxiliary loops 506 and 522 are made of electrically nonconductive material preferably in the form of a synthetic resin or polymeric material such as polythylene or nylon.

In using the snare cauterization instrument assemblies of FIGS. 7–9, cauterization loop 502 or 520 and auxiliary loop 506 or 522 are expanded from a collapsed configuration inside the distal end of sheath member 514 to an expanded configuration. In the expanded configuration, auxiliary loop 506 or 522 is preferably larger than cauterization loop 502 or 520 and essentially parallel thereto. A special case of parallelism is found where the cauterization loop and the auxiliary loop are coplanar.

Pursuant to additional steps in the procedure, pocket or web member 512 is opened during the expansion of cauterization loop 502 or 520 and auxiliary loop 506 or 522 and the expanded loops are passed over a selected polyp or other internal tissue agglomeration to be removed, so that web member 512 substantially surrounds the polyp. Cauterization loop 502 or 520 is then closed by pulling it into the distal end of sheath member 514 or 528 (FIG. 9). The closure of cauterization loop 502 or 506 around a base region of the polyp while the cauterization loop is energized with electrical current serves to sever the polyp at its base. Maintaining web member 512 surrounding the polyp during the cauterization procedure serves to capture the severed polyp at the instant of its severance.

Figure 10:
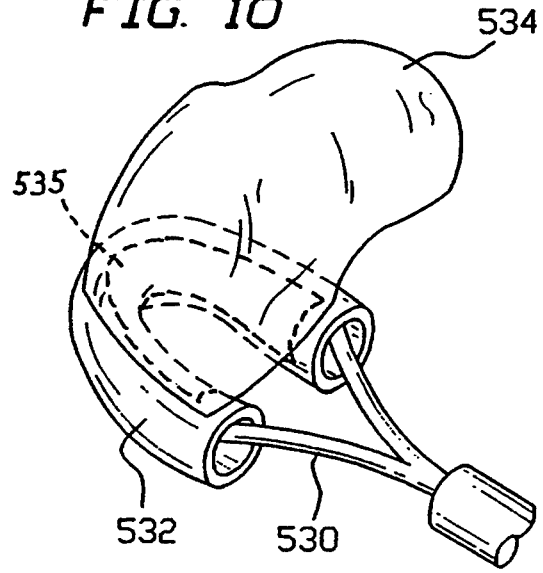
FIG. 10 is a schematic partial perspective view, on an enlarged scale, of an additional snare cauterization instrument assembly in accordance with the present invention.

As illustrated in FIG. 10, a modified snare cauterization assembly includes a cauterization loop 530 surrounded along a substantial portion of its length by a tubular jacket or sleeve 532 to which a flexible pocket-defining web member 534 is connected. Jacket or sleeve 532 is made of a heat-conductive and electricity-conductive material enabling cauterization to proceed through the medium of the sleeve. In addition, sleeve 532 is provided with a coating or layer 535 of a biocompatible dye or ink material of a predetermined color. Color from coating 535 is transferred from the cauterization loop and particularly from sleeve 532 during the conduction of current through the loop. Coating 535 may be a liquifiable solid or a powder. Such a color-transferable coating or layer may be provided directly on any of the cauterization loops described herein. The deposition of a common color on a severed polyp and an unsevered neck or base area serves to facilitate a locating of the polyp's original situs upon a subsequent identification of the polyp as being malignant or a carcinoma. This is especially advantageous where several polyps are caught in the same procedure (see FIG. 15).

Figure 11:
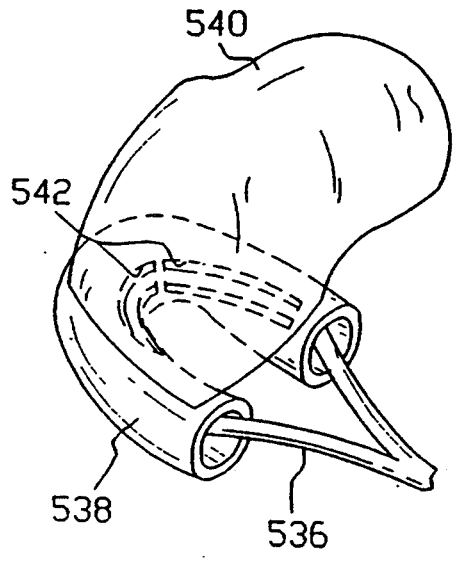
FIG. 11 is a schematic partial perspective view, on an enlarged scale, of yet a further snare cauterization instrument assembly.

As illustrated in FIG. 11, another modified snare cauterization assembly comprises a cauterization loop 536 enclosed along essentially its entire length by a tubular jacket or sleeve. Sleeve 538 is provided along an inner side with a plurality of longitudinally extending windows 542 for facilitating or enabling the conduction of heat and/or electrical current from cauterization loop 536 to organic tissues of a polyp or other cell mass to be removed from a patient's body.

Figure 12:
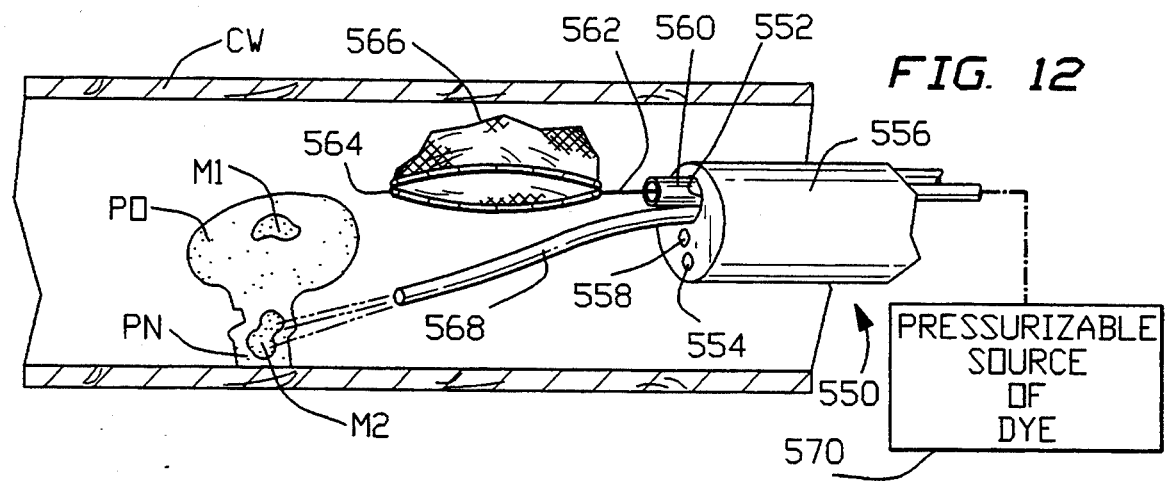
FIG. 12 is a schematic partial cross sectional view of a patient's colon with a polyp, showing a snare cauterization instrument assembly in accordance with the present invention inserted through the biopsy channel of an endoscope which is itself inserted into the patient's colon, and further showing an instrument for depositing color markers on organic tissues.

As shown in FIG. 12, a surgical instrument assembly for use in a snare cauterization operations comprises an endoscope assembly 550 including a biopsy channel 552 and a light outlet 554 at a distal end of an endoscope insertion member 556 for delivering light to a surgical site inside a patient. The distal end of the endoscope insertion member 556 is further provided with a light inlet 558 for receiving light reflected from a surgical site. Light outlet 554 and light inlet 558 are located at the distal ends of a fiber optic illumination guide (not shown) and a fiber optic image guide (not shown), respectively, which extend longitudinally through endoscope insertion member 556.

As further illustrated in FIG. 12, a tubular sheath member 560 is inserted through biopsy channel 552, while a metal wire 562 passes longitudinally through the sheath 560 and is operatively connected at a distal end to an alternately expandable and collapsible metallic cauterization loop 564. An electrical supply (not shown in FIG. 12) is operatively connected to wire 562 for feeding an electrical current to loop 564 via the wire. A manually actuatable shifter (not illustrated in FIG. 12) is operatively connected to wire 562 at a proximal end thereof for longitudinally sliding the wire along sheath 560 in alternately opposite directions. A flexible web member 566 is connected to loop 564 to form a capture pocket, the loop defining a mouth opening of the pocket. Web member 566 is attached to loop 564 in a manner so as to expose the loop to enable effective cauterization of organic tissues by the loop.

Also extending through biopsy channel 552 is a tubular member 568 connected at a proximal end to a pressurizable dye or color source 570 such as a hypodermic syringe filled with a biocompatible liquid of a predetermined hue. A distal end portion of tubular member 568 is ejected from biopsy channel 552 upon arrival of the distal end of endoscope assembly 550 at an internal surgical site where a polyp PO is detected via light outlet 554 and light inlet 558 of endoscope assembly 550. Colored fluid is squirted from tubular member 568 to place recognizable markers M1 and M2 on polyp PO and a lower portion of a polyp neck PN by which polyp PO is connected to a colon wall CW of a patient. Markers M1 and M2 enable subsequent identification of the original location of polyp PO upon a medical analysis of the polyp after it has been severed and removed from the patient in accordance with procedures described herein and other steps known to those skilled in the art.

Upon an insertion of endoscope insertion member 556 into a patient's colon, endoscope assembly 550 is used to visually monitor internal body tissues of the patient, including the internal surface of colon wall CW. Upon detecting selected internal body tissues (e.g., polyp PO) to be removed from the patient, loop 564 and web member 566 are ejected from a distal end of biopsy channel 552. Loop 564 and web member 566 are at least partially expanded from a collapsed configuration upon their ejection from biopsy channel 552. Loop 564 is manipulated from outside of the patient, e.g., via endoscope assembly 550 and more particularly via wire 562 or sheath 560, to pass the expanded loop over the polyp PO so that web member 566 substantially surrounds the polyp. Subsequently, loop 564 is closed to engage the polyp PO around a base region thereof. Closure is effectuated by sliding sheath 560 in a distal direction so that a proximal part of loop 564 is retracted into the sheath. An electrical current is conducted through the closed or partially closed loop 564 to burn through the base region of polyp PO, thereby severing the polyp PO at the base region. Loop 564 is closed further upon a completed burning of the loop through the base of the polyp PO, thereby capturing the severed polyp in web member or pocket 566.

Polyp PO and neck PN may be marked with a biocompatible dye or ink by tubular member 568 prior to the cauterization procedure. Alternatively, at least the neck portion PN may be marked after polyp PO has been severed by loop 564 and captured in web member 566. Tubular member 568 operates to spray a determinable quantity of liquid dye or ink onto the surfaces of polyp PO and neck or base PN.

Figure 13:
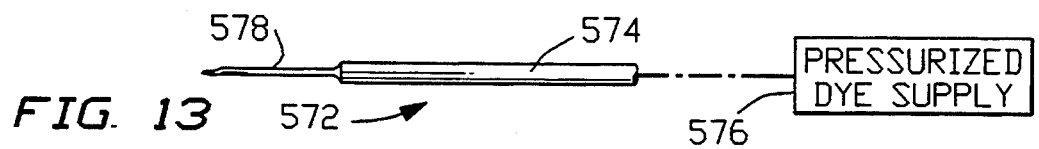
FIG. 13 is partially a schematic partial side elevational view and partially a block diagram of another color deposition instrument alternatively utilizable with the endoscopic snare cauterization instrument assembly of FIG. 12.

As illustrated in FIG. 13, another instrument 572 utilizable with endoscope assembly 550 to mark organic tissues inside a patient comprises a tubular member 574 operatively connected at a proximal end to a pressurized or pressurizable supply 576 of a biocompatible fluidic dye material. At a distal end, tubular member 574 is provided with a needle 578 for use in injecting the dye material below the surface of polyp PO and neck PN.

Figure 14:
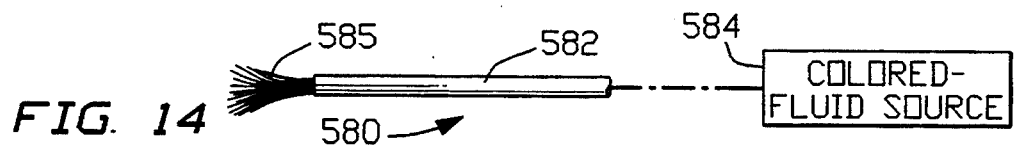
FIG. 14 is partially a schematic partial side elevational view and partially a block diagram of yet another color deposition instrument alternatively utilizable with the endoscopic snare cauterization instrument assembly of FIG. 12.

As shown in FIG. 14, another instrument 580 utilizable with endoscope assembly 550 to mark organic tissues inside a patient comprises a tubular member 582 operatively connected at a proximal end to a pressurized or pressurizable supply 584 of a biocompatible fluidic dye material. At a distal end, tubular member 582 is provided with a brush 585 for use in applying or painting the dye material on the surface of polyp PO and neck PN.

Figure 15:
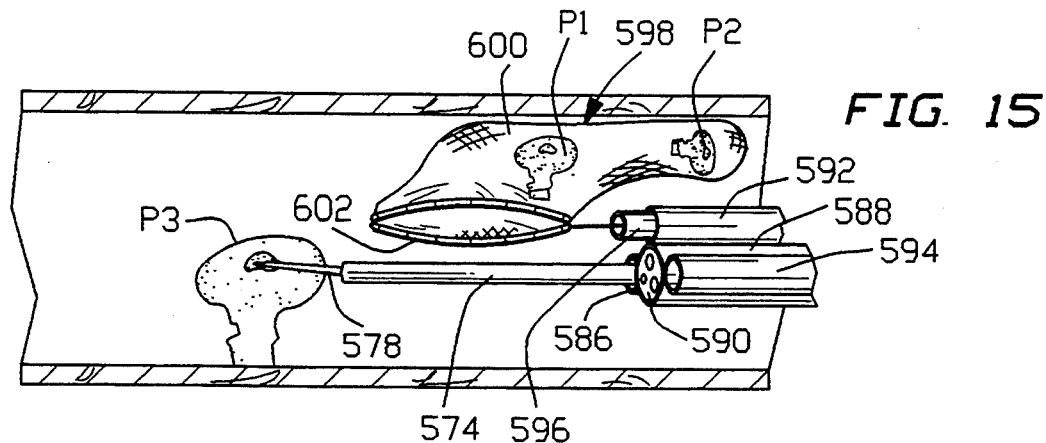
FIG. 15 is a schematic partial cross sectional view of a patient's colon with a polyp, showing a snare cauterization instrument assembly in accordance with the present invention inserted through an alternately collapsible and expandable biopsy channel of an endoscope assembly which is itself inserted into the patient's colon, and further showing an instrument for depositing color markers on organic tissues.

Instrument 572 of FIG. 13 or instrument 580 of FIG. 14 may be inserted through biopsy channel 552 of endoscope assembly 550. Alternatively, tubular member 568 or marking instrument 572 or 580 may be inserted through an alternately expandable and collapsible biopsy channel 586 provided on a sheath 588 surrounding an endoscope insertion member 590, as illustrated in FIG. 15. Such an endoscope sheath 588 may take the form described and illustrated in U.S. Pat. Nos. 4,646,722 and 5,025,778, the disclosures of which are hereby incorporated by reference.

Sheath 588 is provided with other alternately expandable and collapsible biopsy channels 592 and 594, one of which receives a sheath 596 of a cauterization instrument assembly 598. As depicted in FIG. 15, an expanded web member 600 at a distal end of instrument assembly 598 carries a pair of polyps P1 and P2 which have already been marked with respective colors and severed. FIG. 15 shows a third polyp P3 being marked by instrument 572 (FIG. 13) prior to cauterization and severing by a loop 602 to which web member 600 is attached in a manner to enable cauterization by the loop.

Figure 16:
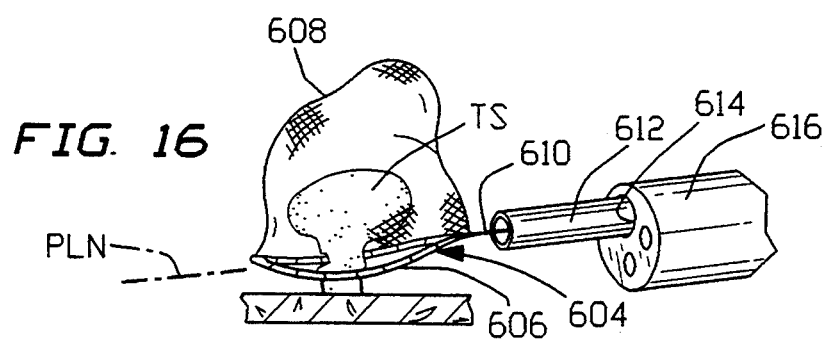
FIG. 16 is a schematic perspective view of a distal end portion of an endoscopic cauterization instrument assembly in accordance with the present invention, showing a cauterization loop of the assembly in use to cauterize and sever a polyp in a patient's colon.

As shown in FIG. 16, another assembly for use in severing and removing an organic tissue sample TS from inside a patient comprises a cauterization loop 604 which in an expanded configuration has a bent configuration which arcs at 606 laterally from a plane PLN in which the loop opens and closes. Arc or curvature 606, inherent in the prestressed or spring-biased construction of loop 604, facilitates the capture of polyps by facilitating the encirclement thereof, as indicated in FIG. 16. The curved design of FIG. 16 may be used in any of the snare embodiments described herein, as well as in prior art cauterization loops without an attached capture pocket or web. Loop 604 is provided with a capture pocket 608 and is operatively connected to an electrical energy source (not shown) via an elongate wire 610 extending longitudinally through a sheath 612 in turn extending through a biopsy channel 614 of an endoscope insertion member 616.

Although the invention has been described in terms of particular embodiments and applications, one of ordinary skill in the art, in light of this teaching, can generate additional embodiments and modifications without departing from the spirit of or exceeding the scope of the claimed invention. For example, colored staples may be used to mark a polyp and/or its base, the staples being applied via an endoscopic stapling instrument as disclosed in U.S. Pat. Nos. 5,015,249 and 5,049,153 and 5,156,609, the disclosures of which are hereby incorporated by reference. The staples may be applied to the base or neck of a severed polyp either before or after a cauterization procedure. Accordingly, it is to be understood that the drawings and descriptions herein are proffered by way of example to facilitate comprehension of the invention and should not be construed to limit the scope thereof.

What is claimed is:

1. A method for removing a selected portion of internal body tissues of a patient, comprising the steps of:
   providing a conductive cauterization loop to which a flexible web member is connected to define an expandable pocket, said web member being attached to said loop in a manner so as to expose said loop to enable effective cauterization of organic tissues by said loop;
   inserting an endoscope assembly into a patient;
   using said endoscope assembly to visually monitor internal body tissues of the patient upon insertion of said endoscope assembly into the patient;
   upon detecting selected internal body tissues to be removed from the patient, ejecting said loop with said web member from a distal end of a biopsy channel of said endoscope assembly;
   upon ejection of said loop and said web member from said biopsy channel, at least partially expanding said loop and said web member from a collapsed configuration;
   manipulating said loop from outside of the patient to pass the expanded loop over the selected internal body tissues to be removed, so that said web member substantially surrounds said selected internal body tissues;
   closing said loop to engage said selected internal body tissues around a base region thereof;
   conducting an electrical current through said loop to burn through said selected internal body tissues at said base region, thereby severing said selected internal body tissues at said base region; and upon a completed burning of said loop through said base region, at least partially closing said loop, thereby capturing the severed internal body tissues.

2. The method defined in claim 1, further comprising the steps of ejecting an auxiliary instrument from a distal end of the endoscope assembly and operating said auxiliary instrument to apply a pair of markers to tissues on opposite sides of said base region, thereby enabling subsequent identification of the severed internal body tissues with a respective site within the patient.

3. The method defined in claim 2 wherein the step of operating includes the step of applying a biocompatible dye or ink to tissues on opposite sides of said base region.

4. The method defined in claim 1, further comprising the step of transferring a color patch from said loop during said step of conducting.

5. A surgical instrument assembly for use in snare cauterization operations, comprising:
   an endoscope assembly including an endoscope insertion member having a biopsy channel and further having means disposed at a distal end of said endoscope insertion member for delivering light to and receiving light from a surgical site;
   a tubular sheath member inserted through said biopsy channel;
   a metallic cauterization loop;
   a metal wire operatively connected to said loop, said wire passing longitudinally through said sheath;
   electrical supply means operatively connected to said wire for feeding an electrical current to sail loop via said wire;
   manually actuatable shifting means operatively connected to said wire for longitudinally sliding said wire along said sheath in alternately opposite directions; and
   a flexible web member connected to said loop to form a capture pocket, said loop defining a mouth opening of said pocket, said web member being attached to said loop in a manner so as to expose said loop to enable effective cauterization of organic tissues by said loop.

6. The instrument assembly defined in claim 5 wherein said loop opens and closes in essentially a single plane.

7. The instrument assembly defined in claim 5 wherein said loop has a bend in an expanded configuration of said loop, said bend arcing out of a plane in which said loop opens and closes.

8. The instrument assembly defined in claim 5, further comprising identification means ejectable in part from a distal end of the endoscope assembly for applying a pair of markers to tissues on opposite sides of said base region, thereby enabling subsequent identification of the severed internal body tissues with a respective site within the patient.

9. The instrument assembly defined in claim 8 wherein said identification means includes means for applying a biocompatible dye or ink to tissues on opposite sides of said base region.

10. The instrument assembly defined in claim 5, further comprising means for transferring a color patch from said loop tissues on opposite sides of said base region during said step of conducting.

11. A method for removing a selected portion of internal body tissues of a patient, comprising the steps of:
   providing a conductive cauterization loop to which a flexible web member is connected to define an expandable pocket, said web member being attached to said loop in a manner so as to expose said loop to enable effective cauterization of organic tissues by said loop;
   at least partially expanding said loop and said web member from a collapsed configuration;
   passing the expanded loop over the selected internal body tissues to be removed, so that said web member substantially surrounds said selected internal body tissues;
   closing said loop to engage said selected internal body tissues around a base region thereof;
   conducting an electrical current through said loop to burn through said selected internal body tissues at said base region, thereby severing said selected internal body tissues at said base region; and
   operating an instrument to apply a pair of markers to tissues on opposite sides of said base region, thereby enabling subsequent identification of the severed internal body tissues with a respective site within the patient.

12. The method defined in claim 11 wherein said markers are colored staples, said step of operating including the step of applying said staples to the tissues on opposite sides of said base region.

13. The method defined in claim 12 wherein said staples are applied prior to said steps of expanding and passing.

14. The method defined in claim 12 wherein said staples are applied after said steps of expanding and passing.

15. The method defined in claim 11 wherein step of operating includes the step of applying a biocompatible dye or ink to tissues on opposite sides of said base region.

16. The method defined in claim 15 wherein said step of applying includes the step of injecting said biocompatible dye or ink into the tissues.

17. The method defined in claim 11 wherein said markers are areas of matching color.

18. The method defined in claim 11 wherein said step of operating includes the step of transferring a color patch from said loop during said step of conducting.

19. The method defined in claim 11, further comprising the steps of:
   inserting an endoscope assembly into a patient;
   using said endoscope assembly to visually monitor internal body tissues of the patient upon insertion of said endoscope assembly into the patient; and
   upon detecting selected internal body tissues to be removed from the patient, ejecting said loop with said web member from a distal end of a biopsy channel of said endoscope assembly,
   said step of expanding being performed upon ejection of said loop and said web member from said biopsy channel, a distal end portion of said instrument being ejected from a biopsy channel of said instrument assembly, said step of operating said instrument being implemented upon ejection of said distal end portion of said instrument.

20. A surgical assembly comprising:
   a tubular sheath member;
   a metallic cauterization loop, said loop having a bend in an expanded configuration of said loop, said bend arcing out of a plane in which said loop opens and closes;

a metal wire operatively connected to said loop, said wire passing longitudinally through said sheath;

electrical supply means operatively connected to said wire for feeding an electrical current to said loop via said wire;

manually actuatable shifting means operatively connected to said wire for longitudinally sliding said wire along said sheath in alternately opposite directions; and a flexible web member connected to said loop to form a capture pocket, said loop defining a mouth opening of said pocket, said web member being attached to said loop in a manner so as to expose said loop to enable effective cauterization of organic tissues by said loop.

* * * * *